United States Patent [19]

Nicolaides et al.

[11] 4,031,069

[45] June 21, 1977

[54] TETRAPEPTIDES

[75] Inventors: Ernest D. Nicolaides; Francis John Tinney; James Clark French, all of Ann Arbor, Mich.

[73] Assignee: Parke, Davis & Company, Detroit, Mich.

[22] Filed: Mar. 1, 1976

[21] Appl. No.: 662,381

[52] U.S. Cl. .............. 260/112.5 LH; 260/112.5 R;
424/177
[51] Int. Cl.$^2$ ...................................... C07C 103/52
[58] Field of Search ........... 260/112.5 R, 112.5 LH

[56] References Cited

UNITED STATES PATENTS 3,725,380  4/1973  Konig et al. ................ 260/112.5 R

OTHER PUBLICATIONS

J. M. Stewart and J. D. Young, "Solid Phase Peptide Synthesis", Freeman and Co., San Francisco, 1969, pp. 9–13.

J. D. Roberts and M. C. Caserio, "Basic Principles of Organic Chemistry", Benjamin, Inc., N.Y., 1965, pp. 531, 563–564.

E. Schroder and K. Lubke, "The Peptides", vol. 1, Academic Press, N.Y., 1965, pp. 79–80.

*Primary Examiner*—Delbert R. Phillips
*Attorney, Agent, or Firm*—Stephen Raines; David B. Ehrlinger; George M. Richards

[57] ABSTRACT

New tetrapeptides having the formula A-$R_1$-Ser(benzyl)-Tyr(benzyl)-$R_2$-$R_3$ wherein A is t-butoxycarbonyl, cyclohexylcarbonyl, benzyloxycarbonyl and p-nitrobenzyloxycarbonyl; $R_1$ is L-Trp, L-Thr(benzyl), L-Met or Gly; Ser(benzyl) is D-Ser(benzyl) or L-Ser(benzyl); Tyr(benzyl) is D-Tyr(benzyl) or L-Tyr(benzyl); $R_2$ is D-Ala, β-Ala, D-Leu or D-Val; and $R_3$ is lower alkoxy, hydrazino, amino, lower alkylamino or di(lower alkyl)amino.

9 Claims, No Drawings

TETRAPEPTIDES

SUMMARY AND DETAILED DESCRIPTION OF THE INVENTION

The present invention relates to new peptide compounds that are useful as luteinizing hormone releasing factor antagonists and to methods for their production. More particularly, the invention relates to new N-protected tetrapeptides that are represented by the formula

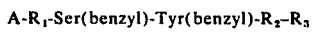

A-R$_1$-Ser(benzyl)-Tyr(benzyl)-R$_2$-R$_3$  I wherein A is t-butoxycarbonyl, cyclohexylcarbonyl, benzyloxycarbonyl or p-nitrobenzyloxycarbonyl, R$_1$ is L-Trp, L-Thr(benzyl), L-Met or Gly; Tyr(benzyl) is L-Tyr(benzyl) or D-Tyr(benzyl), Ser(benzyl) is L-Ser(benzyl) or D-Ser(benzyl), R$_2$ is D-Ala, β-Ala, D-Leu or D-Val and R$_3$ is lower alkoxy, hydrazino, amino, lower alkylamino or di(lower alkyl)amino.

In formula I, the conventional symbols for amino acid residues of peptide compounds linked thereto are used and each is intended to have the following meaning: L-Trp, L-tryptophyl; L-Met, L-methionyl; Gly, glycyl; L-Ser(benzyl), L-seryl(benzyl); D-Ser(benzyl), D-seryl(benzyl); L-Tyr(benzyl), L-tyrosyl(benzyl); D-Tyr(benzyl), D-tyrosyl(benzyl); D-Ala, D-alanyl; β-Ala, β-alanyl; D-Leu, D-leucyl; and D-Val, D-Valyl. In addition, the term "lower alkyl" is intended to mean a straight, branched or cyclic hydrocarbon moiety of up to 6 carbon atoms, such as methyl, ethyl, isopropyl and cyclopropyl and "lower alkoxy" is intended to mean an alkoxy group having a straight, branched or cyclic hydrocarbon moiety of up to 6 carbon atoms, such as methoxy, ethoxy and isopropoxy. These symbols and terms will also be used in the formulae that follow for other compounds and each such symbol or term should be understood to have the meaning given above.

In accordance with this invention, compounds of the formula I, wherein A, R$_1$ and R$_2$ are as previously defined and R$_3$ is lower alkoxy, are produced by removing a protected tetrapeptide from a resin complex of the following structure

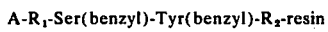

A-R$_1$-Ser(benzyl)-Tyr(benzyl)-R$_2$-resin  II wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected tetrapeptide through a methyleneoxy bridge wherein the methylene group is attached to the polymeric portion of the resin and the oxygen atom is attached to the protected tetrapeptide and A and R$_1$ are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° C. to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein R$_3$ is hydrazino, amino, lower alkylamino or di(lower alkyl)amino may be prepared by reacting compounds of the formula II wherein A, R$_1$ and R$_2$ are as previously defined, with hydrazine, ammonia, lower alkylamine or di(lower alkyl)amine.

The resin complex is suspended in a solvent, such as methanol, ethanol, dimethylformamide, etc., at a temperature of from about 0° to 50° C. for periods of from 12 hours to 10 days. When employing less reactive amines, the preferred solvent is dimethylformamide.

The complex resins of the formula II are prepared by coupling a protected amino acid of the formula

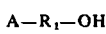

A—R$_1$—OH  III wherein A and R$_1$ are as previously defined, with complex resins of the formula

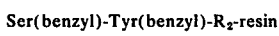

Ser(benzyl)-Tyr(benzyl)-R$_2$-resin  IV in an organic solvent, such as dichloromethane with the aid of dicyclohexylcarbodiimide. The three reactants may be used in about equimolar quantities but excess amounts of the protected amino acid and dicyclohexylcarbodiimide are sometimes advantageous. The reaction is generally conducted at about room temperature for a period of from about fifteen minutes to about 16 hours.

The complex resins of the formula IV are prepared by treating complex resins of the formula

t-butoxycarbonyl-Ser(benzyl)-Tyr(benzyl)-R$_2$-resin  V with a large excess of trifluoroacetic acid utilizing dichloromethane as the solvent at temperatures of from 20° to 30° C. for about 10 minutes, followed by neutralization of the trifluoroacetic acid salt with a base such as triethylamine.

The complex resins of formula V are prepared by coupling

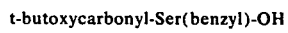

t-butoxycarbonyl-Ser(benzyl)-OH to complex resins of the formula

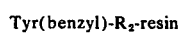

Tyr(benzyl)-R$_2$-resin  VI using the reaction procedure described for the preparation of compounds of the formula II.

The complex resins of the formula VI are prepared by treating the complex resins of the formula

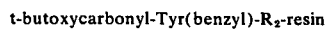

t-butoxycarbonyl-Tyr(benzyl)-R$_2$-resin  VII with trifluoroacetic acid using the reaction procedure for the preparation of compounds of the formula IV.

The complex resins of the formula VII are prepared by coupling

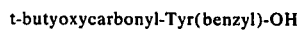

t-butyoxycarbonyl-Tyr(benzyl)-OH to complex resins of the formula

R$_2$-resin  VIII according to the procedure used for the preparation of compounds of the formula II.

The complex resins of the formula VIII are prepared by treating the complex resins of the formula t-butoxycarbonyl-$R_2$-resin with trifluoroacetic acid using the reaction procedure for the preparation of compounds of the formula IV.

In accordance with this invention, compounds of the formula I, wherein A, $R_1$ and $R_2$ are as previously described and $R_3$ is hydrazino, amino, lower alkylamino or di(lower alkyl)amino are prepared by reacting a compound of the formula I wherein $R_3$ is alkoxy, preferably methoxy, with hydrazine, ammonia, lower alkylamine or di(lower alkylamine).

The reactions are conducted at temperatures of from about 5° to 100° C. for from 3 hours to 4 days, preferably about room temperature. Generally, a large excess of hydrazine, preferably used in the form of its hydrate, or amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein A, $R_1$ and $R_2$ are as previously defined and $R_3$ is amino, lower alkylamino or di(lower alkyl)amino are prepared by reacting a compound of the formula A-$R_1$-Ser(benzyl)-Tyr(benzyl)-$R_2$-$N_3$  IX with ammonia, lower alkylamine or di(lower alkyl)amine in a non-reactive solvent such as dimethylformamide, dioxane, tetrahydrofuran or mixtures thereof. The reaction is carried out at about −30° C. to about 0° C. for about 12 to 24 hours, preferably −20° C. to 0° C. for from 16 to 19 hours. The two reactants are used in approximately equimolar amounts although a slight excess of the amine, about 10 percent, is preferred. When A is t-butoxycarbonyl, care should be taken to avoid the presence of a large excess of acid.

The azide compounds of the formula IX are normally prepared in situ by reacting a peptide hydrazide compound of the formula I wherein A, $R_1$ and $R_2$ are as previously defined and $R_3$ is hydrazino, with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature between −30° C. and 0° C. Following the in situ formation of the azide of formula IX and prior to the further reaction of the peptide azide with the appropriate amine to form certain tetrapeptides of formula I, a tertiary amine such as triethylamine is added to the reaction mixture to neutralize the acid used.

Compounds of the formula I wherein A, $R_1$ and $R_2$ are as previously described and $R_3$ is hydrazino, amino, lower alkylamino or di(lower alkyl)amino are prepared by coupling a compound of the formula A-$R_1$-Ser(benzyl)-Tyr(benzyl)-$R_2$-OH  X with hydrazine, ammonia, lower alkylamine or di(lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° to 50° C., preferably room temperature for periods of from 10 hours to 5 days.

1-Hydroxybenzotriazole may also be used in the above reaction in addition to the dicyclohexylcarbodiimide. The 1-hydroxybenzotriazole is added in a ratio of one to two equivlents when compared to the reactants.

The compounds of the formula X are prepared by the hydrolysis of a compound of formula I wherein A, $R_1$ and $R_2$ are as previously defined and $R_3$ is lower alkoxy. The reaction is conducted at temperatures of from 20° C. to 30° C. using about 0.5 ml. of the two normal aqueous sodium hydroxide solution and 10 ml. of solvent, such as water or methanol, for each millimole of ester. The compound of formula X is isolated afer acidification with an aqueous solution of citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Tetrapeptides of this invention were screened for LRF antagonist activity in vitro using rat anterior pituitary cell cultures as described by Vale et al. [Endocrinology, 91, 562 (1972)]. The inhibition of LRF (luteinizing hormone release factor) induced luteinizing hormone (LH) release into the culture medium is the endpoint in this in vitro bioassay.

Following are the results of the above tests on certain preferred compounds.

| ACTIVITY TABLE FOR IN VITRO TEST IN RAT ANTERIOR PITUITARY CELL CULTURES | | |
|---|---|---|
| Molar Conc. | LH Value ng/ml. | % LH Release Inhibition |
| $N^\alpha$-t-butoxycarbonyl-L-tryptophyl-O-benzyl-L-seryl-O-benzyl-L-tyrosyl-D-leucine methyl ester | | |
| 1 × 10⁻⁶ | 35.83 | 54 |
| LRF Control 1 × 10⁻⁹ | 70.11 | |
| Saline Control | 6.62 | |
| 1 × 10⁻⁶ | 14.09 | 81 |
| LRF Control 1 × 10⁻⁹ | 38.46 | |
| Saline Control | 8.27 | |
| $N^\alpha$-cyclohexylcarbonyl-L-tryptophyl-O-benzyl-D-seryl-O-benzyl-L-tyrosyl-D-alanine N-ethylamide | | |
| 1 × 10⁻⁶ | 40.21 | 47 |
| LRF Control 1 × 10⁻⁹ | 70.11 | |
| Saline Control | 6.62 | |
| 1 × 10⁻⁶ | 11.98 | 85 |
| LRF Control 1 × 10⁻⁹ | 27.71 | |
| Saline Control | 9.25 | |
| $N^\alpha$-p-nitrobenzylcarbonyl-glycyl-O-benzyl-L-seryl-O-benzyl-L-tyrosyl-D-alanine methyl ester | | |
| 1 × 10⁻⁶ | 37.24 | 58 |
| LRF Control 1 × 10⁻⁹ | 73.59 | |
| Saline Control | 10.58 | |
| 1 × 10⁻⁶ | 9.60 | 83 |
| LRF Control 1 × 10⁻⁹ | 24.95 | |
| Saline Control | 6.50 | |
| $N^\alpha$-t-butoxycarbonyl-L-tryptophyl-O-benzyl-L- | | |

ACTIVITY TABLE FOR IN VITRO TEST IN RAT ANTERIOR PITUITARY CELL CULTURES

| | Molar Conc. | LH Value ng/ml. | % LH Release Inhibition |
|---|---|---|---|
| seryl-O-benzyl-D-tyrosyl-D-alanine N-ethylamide | $1 \times 10^{-6}$ | 9.32 | 72 |
| LRF Control | $1 \times 10^{-9}$ | 20.28 | |
| Saline Control | | 4.98 | |
| | $1 \times 10^{-6}$ | 33.92 | 63 |
| LRF Control | $1 \times 10^{-9}$ | 73.59 | |
| Saline Control | | 10.58 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, October 29, 1971, pages 511-512. Thus, the tetrapeptides of this invention are useful in controlling ovulation and in restricting fertility.

The invention is illustrated by the following examples.

EXAMPLE 1

$N^{\alpha}$-t-Butoxy-O-benzyl-L-threonyl-O-benzyl-L-seryl-O-benzyl-L-tyrosyl-D-alanine methyl ester Chloromethylated resin cross-linked with 1 percent divinylbenzene, 40 g., $N^{\alpha}$-t-butoxycarbonyl-D-alanine, 14 g. and triethylamine, 7.4 g., in 500 ml. ethanol are refluxed for three days and filtered off. A 12 g., 8.4 mmol portion of the $N^{\alpha}$-t-butoxycarbonyl-D-alanine resin, thus obtained, is deprotected by treatment with a 50 percent trifluoroacetic acid in dichloromethane solution, 250 ml. for 10 minutes at room tempeature, followed by filtration, treatment with a cold mixture of 30 ml. of triethylamine in 250 ml. dichloromethane and mixing for five minutes. The resin is filtered off and washed with dichloromethane. 250 ml., three times. $N^{\alpha}$-t-butoxycarbonyl-O-benzyl-L-tyrosine, 4 g., 11 mmol, in dichloromethane, 100 ml., is added to the above product and after thirty minutes of shaking, dicyclohexylcarbodiimide, 2 g., in dichloromethane, 50 ml., is added and the mixture agitated for four hours. The flask is drained and the resin washed three times with dichloromethane (250 ml. each). Again a 50 percent trifluoroacetic acid in dichloromethane solution (250 ml.) is used as above to remove the t-butoxycarbonyl protecting group and the resin drained and washed as before. Triethylamine, 30 ml. in 250 ml. of cold dichloromethane, is used to liberate the O-benzyl-L-tyrosyl-D-alanine resin, which is treated with $N^{\alpha}$-t-butoxycarbonyl-O-benzyl-L-serine, 3 g., 10 mmol, in dichloromethane (100 ml.) and agitated for 30 minutes. After adding dicyclohexylcarbodiimide, 2 g., in dichloromethane, 50 ml., the reaction mixture is rocked for 4 hours, the flask drained and the resin washed two times with dichloromethane (250 ml. each). The resulting resin (10 g.) is next treated with a 50 percent trifluoroacetic acid in dichloromethane solution (250 ml.) as above to remove the t-butoxycarbonyl protecting group and the resin drained and washed as before. Triethylamine, 30 ml. in 250 ml. of cold dichloromethane, is used to give the free base, O-benzyl-L-seryl-O-benzyl-L-tyrosyl-D-alanine resin which is next treated with $N^{\alpha}$-t-butoxycarbonyl-O-benzyl-L-threonine, 2.5 g., 8.09 mmol in dichloromethane (100 ml.) and agitated for 30 minutes. After adding dicyclohexylcarbodiimide, 1.8 g., 8.7 mmol in dichloromethane, 50 ml., the reaction mixture is rocked for 4 hours, the flask drained and washed two times with dichloromethane (250 ml. each) and dried giving 10.5 g. of $N^{\alpha}$-t-butoxycarbonyl-O-benzyl-L-threonyl-O-benzyl-L-seryl-O-benzyl-L-tyrosyl-D-alanine resin. This product, after being washed with ethanol and then with ether and dried at 50° C. at reduced pressure, is stirred with methanol, 200 ml., in the presence of triethylamine, 20 ml., for sixteen hours, filtered and the volatile components evaporated. The residue, upon treatment with petroleum ether, gives a white solid product, 1.9 g., m.p. 121°-122° C.

EXAMPLE 2

$N^{\alpha}$-t-Butoxycarbonyl-O-benzyl-L-threonyl-O-benzyl-L-seryl-O-benzyl-L-tyrosyl-D-alanine N-ethylamide The methyl ester of Example 1, 400 mg., is dissolved in methanol, 20 ml., and treated with ethylamine, 5 ml., for a period of 3 days at room temperature in a closed container. The volatile components are removed and the product solidified in cyclohexane, 300 mg., m.p. 180°-182° C.

EXAMPLE 3

$N^{\alpha}$-t-Butoxycarbonyl-L-tryptophyl-O-benzyl-L-seryl-O-benzyl-L-tyrosyl-D-alanine methyl ester $N^{\alpha}$-t-Butoxycarbonyl-L-tryptophyl-O-benzyl-L-seryl-O-benzyl-L-tyrosyl-D-alanine resin is prepared from 23 g., 14 mmol. of $N^{\alpha}$-t-butoxycarbonyl-D-alanine resin by successive coupling, according to the general process for solid phase synthesis given in Example 1 with (1) 7 g., 19 mmol, of $N^{\alpha}$-t-butoxycarbonyl-O-benzyl-L-tyrosine and 4 g., 19.4 mmol, of dicyclohexylcarbodiimide, (2) 6 g., 19.7 mmol, of $N^{\alpha}$-t-butoxycarbonyl-O-benzyl-L-serine and 4 g. of dicyclohexylcarbodiimide, and (3) 6 g., 19.7 mmol, of $N^{\alpha}$-t-butoxycarbonyl-L-tryptophan and 4 g. of dicyclohexylcarbodiimide. The resin thus obtained, 30 g., is stirred for 20 hours with 600 ml. of methanol and 50 ml. of triethylamine. The solution is filtered and evaporated. The residue is solidified by trituration in ether; 8 grams; m.p. 93°-94° C.

EXAMPLE 4

$N^{\alpha}$-Butoxycarbonyl-L-tryptophyl-O-benzyl-L-seryl-O-benzyl-L-tyrosyl-D-alanyl hydrazide $N^{\alpha}$-t-Butoxycarbonyl-L-tryptophyl-O-benzyl-L-seryl-O-benzyl-L-tyrosyl-D-alanine methyl ester, 200 mg., is dissolved in 30 ml. of ethanol, treated with 2 ml. of hydrazine hydrate and the solution warmed at 45° C. for 30 minutes and let stand for 24 hours. The solution is evaporated and the residue triturated with ether to give a white solid. This product is further purified by precipitation from ethanol yielding 125 mg.; m.p. 186°-187° C.

EXAMPLE 5

N$^\alpha$-Cyclohexylcarbonyl-L-tryptophyl-O-benzyl-L-seryl-O-benzyl-L-tyrosyl-D-alanine methyl ester

N$^\alpha$-t-Butoxycarbonyl-L-tryptophyl-O-benzyl-L-seryl-O-benzyl-L-tyrosyl-D-alanine methyl ester, 1 g., 12 mmol, is treated with trifluoroacetic acid-dichloromethane (1:1) for 10 to 15 minutes and the solution evaporated. The residue is dissolved in 20 ml. of dimethylformamide, cooled to 5° C. and treated with 0.25 ml. of triethylamine. The solution is then treated with 155 mg., 12.1 mmol, of cyclohexane carboxylic acid, 185 mg., 12.1 mmol, of 1-hydroxybenzotriazole and 250 mg., 12.1 mmol, of dicyclohexylcarbodiimide. The solution is kept at 5° C. for 2 hours and for 44 hours at 25° C. The solution is evaporated and the residue solidified by addition of ether. The product is precipitated from isopropanol as a white solid; 670 mg.; m.p. 181°–183° C.

EXAMPLE 6

N$^\alpha$-Cyclohexylcarbonyl-L-tryptophyl-O-benzyl-L-seryl-O-benzyl-L-tyrosyl-D-alanyl hydrazide

N$^\alpha$-Cyclohexylcarbonyl-L-tryptophyl-O-benzyl-L-seryl-O-benzyl-L-tyrosyl-D-alanine methyl ester, 500 mg., is dissolved in 20 ml. of methanol and treated with 3 ml. of hydrazine hydrate. The solution is warmed to 50° C. for 30 minutes and kept at 25° C. for 20 hours. The precipitated solid is separated by filtration, washed with ethanol and ether, and dried; 450 mg.; m.p. 220°–222° C.

EXAMPLE 7

N$^\alpha$-t-Butoxycarbonyl-L-tryptophyl-O-benzyl-D-seryl-O-benzyl-L-tyrosyl-D-alanine methyl ester

N$^\alpha$ t-Butoxycarbonyl-L-tryptophyl-O-benzyl-D-seryl-O-benzyl-L-tyrosyl-D-alanine resin is prepared from 8 g. of N$^\alpha$-t-butoxycarbonyl-O-benzyl-L-tyrosyl-D-alanine resin by successive coupling, according to the general process for solid phase synthesis given in Example 1, with (13 g., 9.8 mmol, of N$^\alpha$-t-butoxycarbonyl-O-benzyl-D-serine and 2 g., 9.7 mmol, of dicyclohexylcarbodiimide and (2) 3 g., 9.8 mmol, of N$^\alpha$-t-butoxycarbonyl-L-tryptophan and 2 g. of dicyclohexylcarbodiimide. The resin is washed with ethanol and dried. It is then stirred for twenty-four hours at 25° C. with 200 ml. of methanol and 20 ml. of triethylamine. The mixture is filtered and the methanol solution evaporated. The residue is solidified from ether-petroleum ether; 2 g.; m.p. 155°–156° C.

N$^\alpha$-t-Butoxycarbonyl-O-benzyl-L-tyrosyl-D-alanine resin is obtained from 49 g., 35 mmol, of N$^\alpha$-t-butoxycarbonyl-D-alanine resin by coupling, according to the general process of solid phase synthesis given in Example 1, with 15 g., 40 mmol, of N$^\alpha$-t-butoxycarbonyl-O-benzyl-L-tyrosine and 8 g., 38.8 mmol, of dicyclohexylcarbodiimide. The resin is removed, washed with chloroform, ethanol and ether and dried in air; 53 g.

EXAMPLE 8

N$^\alpha$-t-Butoxycarbonyl-L-tryptophyl-O-benzyl-D-seryl-O-benzyl-L-tyrosyl-D-alanyl hydrazide

N$^\alpha$-t-Butoxycarbonyl-L-trypthophyl-O-benzyl-D-seryl-O-benzyl-L-tyrosyl-D-alanine methyl ester, 300 mg., is dissolved in 40 ml. of methanol and treated with 3 ml. of hydrazine hydrate. The solution is heated to reflux for ten minutes and let stand at 25° C. for 18 hours. The precipitated product is separated by filtration, washed with ethanol and dried; 250 mg.; m.p. 177°–178° C.

EXAMPLE 9

N$^\alpha$-t-Butoxycarbonyl-L-tryptophyl-O-benzyl-D-seryl-O-benzyl-L-tyrosyl-D-alanine N-ethylamide

N$^\alpha$-t-Butoxycarbonyl-L-tryptophyl-O-benzyl-D-seryl-O-benzyl-L-tyrosyl-D-alanine methyl ester, 350 mg., is dissolved in 15 ml. of methanol and 5 ml. of dimethylformamide. The solution is treated with 5 ml. of ethylamine and kept at 25° C. for 24 hours. The solution is evaporated and the residue treated with ether to give the product in the form of a white solid; 330 mg.; m.p. 161°–162° C.

EXAMPLE 10

N$^\alpha$-t-Butoxycarbonyl-L-tryptophyl-O-benzyl-L-seryl-O-benzyl-D-tyrosyl-D-alanine methyl ester

N$^\alpha$-t-Butoxycarbonyl-L-tryptophyl-O-benzyl-L-seryl-O-benzyl-D-tyrosyl-D-alanine resin (25 g.), is treated with 50 ml. of triethylamine and 500 ml. of methanol for 2 days at room temperature. The product is chromatographed on silica gel with chloroform-methanol-water (60:30:5) to give 6.6 g.; m.p. 95°–100° C.

N$^\alpha$-t-Butoxycarbonyl-L-tryptophyl-O-benzyl-L-seryl-O-benzyl-D-tyrosyl-D-alanine resin is obtained according to the procedure of Example 1 by treating 20 g. of N$^\alpha$-t-butoxycarbonyl-D-alanine resin, 0.0132 mol, with 7.4 g., 0.02 mol, of N-t-butoxycarbonyl-O-benzyl-D-tyrosine and 4.1 g., 0.02 mol, of dicyclohexylcarbodiimide, (2) 6.0 g., 0.02 mol, of N$^\alpha$-t-butoxycarbonyl-O-benzyl-L-serine and 4.1 g. of dicyclohexylcarbodiimide, and (3) 6.1 g. of N$^\alpha$-t-butoxycarbonyl-L-tryptophan and 4.1 g. of dicyclohexylcarbodiimide.

EXAMPLE 11

N$^\alpha$-t-Butoxycarbonyl-L-tryptophyl-O-benzyl-L-seryl-O-benzyl-D-tyrosyl-D-alanyl hydrazide

The methyl ester of Example 10, 300 mg., is treated with 1 g. of hydrazine hydrate in 150 ml. of methanol for 2 days at room temperature. The resultant product is chromatographed on silica gel with chloroform-methanol-water (60:30:5) to yield 0.14 g.; m.p. 210°–213° C.

EXAMPLE 12

N$^\alpha$-t-Butoxycarbonyl-L-tryptophyl-O-benzyl-L-seryl-O-benzyl-D-tyrosyl-D-alanine N-ethylamide

The methyl ester of Example 10, 300 mg., is treated with 5 g. of ethylamine in 100 ml. of methanol for 4 days at room temperature. The product from evaporation is triturated with ether to yield 0.15 g. of product, m.p. 134°–139° C.

EXAMPLE 13

N$^\alpha$-t-Butoxycarbonyl-L-tryptophyl-O-benzyl-L-seryl-O-benzyl-D-tyrosyl-D-alaninamide

The methyl ester of Example 10, 300 mg., is dissolved in 100 ml. of methanol saturated with ammonia and kept for 4 days at room temperature. The crude product is chromatographed on silica gel in chloroform-methanol-water (60:30:5) to yield 0.14 g.; m.p. 180°–185° C.

EXAMPLE 14

$N^\alpha$-t-Butoxycarbonyl-L-tryptophyl-O-benzyl-L-seryl-O-benzyl-L-tyrosyl-β-alanine methyl ester $N^\alpha$-t-Butoxycarbonyl-L-tryptophyl-O-benzyl-L-seryl-O-benzyl-L-tyrosyl-β-alanine resin, 4.6 g., is converted to the corresponding methyl ester by treatment with 90 ml. of methanol and 10 ml. of triethylamine at room temperature for 24 hours. The evaporation residue crystallizes from 10 ml. of methanol, 1.16 g.; m.p. 165°–167° C.

$N^\alpha$-t-Butoxycarbonyl-L-tryptophyl-O-benzyl-L-seryl-O-benzyl-L-tyrosyl-β-alanine resin is obtained according to the procedure of Example 1 from N-t-butoxycarbonyl-β-alanine resin, 25 g., 21.7 mmol, in successive reaction with (1) 9.75 g., 26.2 mmol, of $N^\alpha$-t-butoxycarbonyl-O-benzyl-L-tyrosine and 6 g., 29 mmol of dicyclohexylcarbodiimide, (2) 7.8 g., 26.2 mmol, of $N^\alpha$-t-butoxycarbonyl-O-benzyl-L-serine and 6.5 g. of dicyclohexylcarbodiimide, then 2.0 g., 6.8 mmol, of $N^\alpha$-t-butoxycarbonyl-O-benzyl-L-serine and 1.5 g. of dicyclohexylcarbodiimide and (3) 9.9 g., 32.6 mmol, of $N^\alpha$-t-butoxycarbonyl-L-tryptophan in 10 ml. of dimethylformamide and 7.5 g., 36.4 mmol, of dicyclohexylcarbodiimide with deblocking prior to each coupling step using dichloromethane-trifluoroacetic acid (60:40).

N-t-Butoxycarbonyl-β-alanine resin is obtained by the procedure given in Example 1 using 50 g. of chloromethylated resin (Bio-Rad) with 14 g. of N-t-butoxycarbonyl-β-alanine, m.p. 77°–79° (from β-alanine and t-butoxycarbonyl azide), 120 ml. of absolute ethanol and 9.5 ml. of triethylamine and refluxing for 48 hours. Nitrogen analysis indicates 0.87 mmol N-t-butoxycarbonyl-β-alanine per gram of resin.

EXAMPLE 15

$N^\alpha$-t-Butoxycarbonyl-L-tryptophyl-O-benzyl-L-seryl-O-benzyl-L-tyrosyl-β-alanyl hydrazide The methyl ester of Example 14, 152 mg., in 1 ml. of dimethylformamide and 4 ml. of methanol is treated with 0.21 ml. of hydrazine hydrate at room temperature for 4 days. The residue from evaporation is crystallized from methanol and washed with ethyl acetate and then pentane, giving 142 mg. of product; m.p. 183°–187° C.

EXAMPLE 16

$N^\alpha$-t-Butoxycarbonyl-L-tryptophyl-O-benzyl-L-seryl-O-benzyl-L-tyrosyl-β-alanine N-ethylamide The methyl ester of Example 14, 151 mg., is treated with 1 ml. of dimethylformamide and 25 ml. of 9 molar ethylamine in methanol. After 68 hours at room temperature, the solution is evaporated and the residue crystallized from methanol. The resultant product is washed with ethyl acetate and methanol; 137 mg.; m.p. 181°–184° C.

EXAMPLE 17

$N^\alpha$-t-Butoxycarbonyl-L-tryptophyl-O-benzyl-L-seryl-O-benzyl-L-tyrosyl-D-leucine methyl ester $N^\alpha$-t-Butoxycarbonyl-D-leucine resin, 12 g., is reacted according to the procedure of Example 1, successively with (1) 5 g., 13.5 mmol, of $N^\alpha$-t-butoxycarbonyl-O-benzyl-L-tyrosine and 2.8 g., 13.5 mmol, of dicyclohexylcarbodiimide, (2) 4.1 g., 13.5 mmol, of $N^\alpha$-t-butoxycarbonyl-O-benzyl-L-serine and 2.8 g. of dicyclohexylcarbodiimide and (3) 4.1 g., 13.5 mmol, of $N^\alpha$-t-butoxycarbonyl-L-tryptophan and 2.8 g. of dicyclohexylcarbodiimide. The resulting tetrapeptide resin is stirred for 16 hours with 200 ml. of methanol and 20 ml. of triethylamine after being washed from the reaction flask with ethanol. The yellow solid obtained by evaporation is precipitated from isopropanol by cooling to give a white product; 3.15 g.; m.p. 136°–137° C.

$N^\alpha$-t-Butoxycarbonyl-D-leucine resin is obtained from 10 g. of chloromethylated resin, 3.5 g. of $N^\alpha$-t-butoxycarbonyl-D-leucine and 2.3 ml. of triethylamine after 2 days at reflux in 200 ml. of ethanol; 12 g.; 0.79 mmol of $N^\alpha$-t-butoxycarbonyl-D-leucine per gram of resin.

EXAMPLE 18

$N^\alpha$-t-Butoxycarbonyl-L-tryptophyl-O-benzyl-L-seryl-O-benzyl-L-tyrosyl-D-leucyl hydrazide The methyl ester of Example 17 is reacted with 3 ml. of hydrazine hydrate in 20 ml. of dimethylformamide for 2 days at 25° C., giving 300 mg. of the product; m.p. 189°–190° C.

EXAMPLE 19

$N^\alpha$-t-Butoxycarbonyl-L-tryptophyl-O-benzyl-L-seryl-O-benzyl-L-tyrosyl-D-leucine N-ethylamide The methyl ester of Example 17 is reacted with 5 ml. of ethylamine, 15 ml. of methanol and 5 ml. of dimethylformamide at 25° C. for 24 hours. Evaporation and trituration of the residue with ether gives 400 mg. of the product; m.p. 196°–198° C.

EXAMPLE 20

$N^\alpha$-t-Butoxycarbonyl-L-tryptophyl-O-benzyl-L-seryl-O-benzyl-L-tyrosyl-D-valine methyl ester $N^\alpha$-t-Butoxycarbonyl-L-tryptophyl-O-benzyl-L-seryl-O-benzyl-L-tyrosyl-D-valine resin is prepared according to the procedure of Example 1 from $N^\alpha$-t-butoxycarbonyl-D-valine resin, 11 g., 5 mmol, reacted successively with (1) 3.5 g., 9.4 mmol, of $N^\alpha$-t-butoxycarbonyl-O-benzyl-L-tyrosine and 2 g., 9.7 mmol, of dicyclohexylcarbodiimide, (2) 3 g., 9.8 mmol, of $N^\alpha$-t-butoxycarbonyl-O-benzyl-L-serine and 2 g. of dicyclohexylcarbodiimide and (3) 3 g., 9.85 mmol, of $N^\alpha$-t-butoxycarbonyl-L-tryptophan and 2 g. of dicyclohexylcarbodiimide.

The resin thus obtained, 11.5 g., is stirred for 18 hours at 25° C. with 200 ml. of methanol and 20 ml. of triethylamine followed by filtration and evaporation. The product, obtained from the evaporated filtrate, is precipitated from isopropanol by cooling to give a white solid, 500 mg.; m.p. 98°–100° C.

$N^\alpha$-t-Butoxycarbonyl-D-valine resin is obtained by the procedure of Example 1 from 10 g. of chloromethylated resin, 3 g., 13.8 mmol, of $N^\alpha$-t-butoxycarbonyl-D-valine and 1.9 ml. of triethylamine. The mixture is refluxed for five days yielding 11 g., 0.45 mmol of $N^\alpha$-t-butoxycarbonyl-D-valine of resin per gram of resin.

EXAMPLE 21

N$^\alpha$-t-Butoxycarbonyl-L-tryptophyl-O-benzyl-L-seryl-O-benzyl-L-tyrosyl-D-valine N-ethylamide The methyl ester of Example 20, 300 mg., is mixed with 30 ml. of methanol and 10 ml. of ethylamine and kept at 25° C. for 5 days. A white solid is obtained by evaporation and trituration of the residue with ether; 150 mg.; m.p. 213°–214° C.

EXAMPLE 22

N$^\alpha$-Cyclohexylcarbonyl-L-tryptophyl-O-benzyl-L-seryl-O-benzyl-D-tyrosyl-D-alanine methyl ester L-Tryptophyl-O-benzyl-L-seryl-O-benzyl-D-tyrosyl-D-alanine methyl ester trifluoroacetic acid salt, 0.8 g., 0.96 mmol, is reacted with 0.11 g. of triethylamine to neutralize, followed by 0.13 g., 0.98 mmol, of cyclohexane carboxylic acid, 0.21 g., 1.02 mmol, of dicyclohexylcarbodiimide and 0.153 g., 1 mmol, of 1-hydroxybenztriazole at room temperature for three days. The reaction mixture is filtered and evaporated to yield 0.14 g. of product; m.p. 165°–168° C.

N$^\alpha$-t-Butoxycarbonyl-L-tryptophyl-O-benzyl-L-seryl-O-benzyl-D-tyrosyl-D-alanine methyl ester, 1 g., (Example 10) is dissolved in cold trifluoroacetic acid and let stand for ten minutes. The L-tryptophyl-O-benzyl-L-seryl-O-benzyl-D-tyrosyl-D-alanine methyl ester trifluoroacetic acid salt is precipitated by addition of ether and is collected on a filter, washed well with ether and dried; 0.9 g.; m.p. 182°–186° C.

EXAMPLE 23

N$^\alpha$-Cyclohexylcarbonyl-L-tryptophyl-O-benzyl-L-seryl-O-benzyl-D-tyrosyl-D-alaninamide The methyl ester of Example 22, 0.15 g., is dissolved in 100 ml. of methanol which has been saturated with ammonia and let stand for 2 days at room temperature. The product is chromatographed on silica gel with chloroform-methanol-water (60:30:5). After removal of the solvent by evaporation, the product, 0.1 g., is obtained as a hemi-hydrate; m.p. 198°–202° C.

EXAMPLE 24

N$^\alpha$-Cyclohexylcarbonyl-L-tryptophyl-O-benzyl-L-seryl-O-benzyl-D-tyrosyl-D-alanine N-ethylamide The methyl ester of Example 22, 200 mg., is reacted with 5 ml. of ethylamine in 100 ml. of methanol at room temperature for 4 days. The product, 0.12 g., is obtained by evaporation and trituration with ether; monohydrate; m.p. 190°–195° C.

EXAMPLE 25

N$^\alpha$-Cyclohexylcarbonyl-L-tryptophyl-O-benzyl-L-seryl-O-benzyl-L-tyrosyl-D-leucine methyl ester N$^\alpha$-t-Butoxycarbonyl-L-tryptophyl-O-benzyl-L-seryl-O-benzyl-L-tyrosyl-D-leucine methyl ester (Example 17), 1 g., 1.16 mmol, is reacted according to the appropriate part of Example 1 with 20 ml. of trifluoroacetic acid, neutralized with triethylamine and coupled with 150 mg., 1.17 mmol, of cyclohexane carboxylic acid using 180 mg., 1.17 mmol, of 1-hydroxybenzotriazole and 240 mg., 1.17 mmol, of dicyclohexylcarbodiimide. The solution is evaporated and the residue triturated with ether. The product is precipitated from isopropanol on cooling as a cream solid; 1 g.; m.p. 158°–160° C.

EXAMPLE 26

N$^\alpha$-Cyclohexylcarbonyl-L-tryptophyl-O-benzyl-D-seryl-O-benzyl-L-tyrosyl-D-alanine methyl ester N$^\alpha$-t-Butoxycarbonyl-L-tryptophyl-O-benzyl-D-seryl-O-benzyl-L-tyrosyl-D-alanine methyl ester (Example 7), 700 mg., 0.85 mmol, is reacted according to the appropriate part of Example 1 with 20 ml. of trifluoroacetic acid and neutralized with triethylamine. The product is coupled with 110 mg., 0.85 mmol, of cyclohexane carboxylic acid, using 130 mg., 0.85 mmol of 1-hydroxybenzotriazole and 175 mg., 0.85 mmol, of dicyclohexylcarbodiimide for two days at 25° C. The mixture is filtered and the solution evaporated to yield a tan solid which is precipitated twice from cooling isopropanol; 200 mg.; m.p. 212°–213° C.

EXAMPLE 27

N$^\alpha$-Cyclohexylcarbonyl-L-tryptophyl-O-benzyl-D-seryl-O-benzyl-L-tyrosyl-D-alanine N-ethylamide The methyl ester of Example 26, 300 mg., is reacted with 10 ml. of ethylamine in 20 ml. of methanol at 25° C. for 2 days. Evaporation and trituration with ether gives a light cream solid; 260 mg.; m.p. 188°–190° C.

EXAMPLE 28

N$^\alpha$-p-Nitrobenzyloxycarbonyl-glycyl-O-benzyl-L-seryl-O-benzyl-L-tyrosyl-D-alanine methyl ester N$^\alpha$-t-Butoxycarbonyl-O-benzyl-L-seryl-O-benzyl-L-tyrosyl-D-alanine resin, 10 g., is treated according to the last deprotecting and coupling steps of Example 1 with 2 g., 8.2 mmol, of N$^\alpha$-p-nitrobenzyloxycarbonyl-glycine in dimethylformamide and dichloromethane and 1.8 g., 8.2 mmol, of dicyclohexylcarbodiimide.

The tetrapeptide resin thus obtained, 11 g., is reacted with 200 ml. of methanol and 20 ml. of triethylamine. After filtration and removal of the volatile components, the crude product is triturated with petroleum ether and precipitated from cooling isopropanol; 2.1 g.; m.p. 136°–137° C.

N$^\alpha$-p-Nitrobenzyloxycarbonyl-glycine is obtained by the procedure of Carpenter and Gish, J. Am. Chem. Soc., 74, 3818 (1952) as a faint yellow solid, 94% yield, m.p. 118°–120° C.

N$^\alpha$-t-Butoxycarbonyl-O-benzyl-L-seryl-O-benzyl-L-tyrosyl-D-alanine resin is prepared according to the procedure of Example 3 except that the reaction sequence is terminated prior to the deprotection and addition of N$^\alpha$-t-butoxycarbonyl-L-tryptophan.

EXAMPLE 29

N$^\alpha$-t-Butoxycarbonyl-L-methionyl-O-benzyl-L-seryl-O-benzyl-L-tyrosyl-D-alanine methyl ester N$^\alpha$-t-Butoxycarbonyl-D-alanine resin, 11 g., 7 mmol, is reacted successively according to the procedure of Example 1 with (1) 3 g., 8 mmol, of N$^\alpha$-t-butoxycarbonyl-O-benzyl-L-tyrosine and 1.7 g., 8 mmol, dicyclohexylcarbodiimide, (2) 2.5 g., 8 mmol, of N$^\alpha$-t-butoxycarbonyl-O-benzyl-L-serine and 1.7 g. of dicyclohexylcarbodiimide and (3) 2 g., 8 mmol, of N$^\alpha$-t-butoxycarbonyl-L-methionine and 1.7 g. of dicyclohexylcarbodiimide.

The resultant tetrapeptide resin, 12.5 g., is reacted according to the procedure of Example 1 with 200 ml. of methanol and 20 ml. of triethylamine. After filtration and evaporation, the crude product is obtained

EXAMPLE 30

N$^\alpha$-t-Butoxycarbonyl-L-methionyl-O-benzyl-L-seryl-O-benzyl-L-tyrosyl-D-alanine N-ethylamide The methyl ester of Example 29, 350 mg., is treated with 5 ml. of ethylamine in 100 ml. of methanol. After evaporation the product is triturated with ether to give a white solid; 240 mg.; m.p. 190°–192° C.

EXAMPLE 31

N$^\alpha$-t-Butoxycarbonyl-L-methionyl-O-benzyl-L-seryl-O-benzyl-L-tyrosyl-D-alanyl hydrazide The methyl ester of Example 29, 350 mg., is treated with 3 ml. of hydrazine hydrate in 40 ml. of methanol, the solution boiled for 10 minutes and let stand for 18 hours. The white precipitate is separated, washed with ethanol and dried; 250 mg.; m.p. 210°–212° C.

We claim:

1. A tetrapeptide represented by the formula

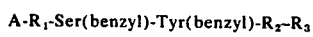

A-R$_1$-Ser(benzyl)-Tyr(benzyl)-R$_2$-R$_3$ wherein A is t-butoxycarbonyl, cyclohexylcarbonyl, benzyloxycarbonyl or p-nitrobenzyloxycarbonyl, R$_1$ is L-Trp, L-Thr(benzyl), L-Met or Gly; Tyr(benzyl) is L-Tyr(benzyl) or D-Tyr(benzyl), Ser(benzyl) is L-Ser(benzyl) or D-Ser(benzyl), R$_2$ is D-Ala, β-Ala, D-Leu or D-Val and R$_3$ is lower alkoxy, hydrazino, amino, lower alkylamino or di(lower alkyl)amino.

2. The compound of claim 1 having the name N$^\alpha$-t-Butoxycarbonyl-L-tryptophyl-O-benzyl-D-seryl-O-benzyl-L-tyrosyl-D-alanine methyl ester.

3. The compound of claim 1 having the name N$^\alpha$-t-Butoxycarbonyl-L-tryptophyl-O-benzyl-L-seryl-O-benzyl-D-tyrosyl-D-alanine N-ethylamide.

4. The compound of claim 1 having the name N$^\alpha$-t-Butoxycarbonyl-L-tryptophyl-O-benzyl-L-seryl-O-benzyl-L-tyrosyl-β-alanyl hydrazide.

5. The compound of claim 1 having the name N$^\alpha$-t-Butoxycarbonyl-L-tryptophyl-O-benzyl-L-seryl-O-benzyl-L-tyrosyl-D-leucine methyl ester.

6. The compound of claim 1 having the name N$^\alpha$-t-Butoxycarbonyl-L-tryptophyl-O-benzyl-L-seryl-O-benzyl-L-tyrosyl-D-valine methyl ester.

7. The compound of claim 1 having the name N$^\alpha$-Cyclohexylcarbonyl-L-tryptophyl-O-benzyl-D-seryl-O-benzyl-L-tyrosyl-D-alanine N-ethylamide.

8. The compound of claim 1 having the name N$^\alpha$-p-Nitrobenzyloxycarbonyl-glycyl-O-benzyl-L-seryl-O-benzyl-L-tyrosyl-D-alanine methyl ester.

9. The compound of claim 1 having the name N$^\alpha$-t-Butoxycarbonyl-L-methionyl-O-benzyl-L-seryl-O-benzyl-L-tyrosyl-D-alanine methyl ester.

* * * * *